(12) United States Patent  
Filipon et al.

(10) Patent No.: US 11,590,318 B2  
(45) Date of Patent: Feb. 28, 2023

(54) CANNULA HAVING A WIRE THAT EXTENDS ALONG SAID CANNULA

(71) Applicant: Xenios AG, Heilbronn (DE)

(72) Inventors: Sven Filipon, Heilbronn (DE); Ozan Wagner, Offenau (DE)

(73) Assignee: Xenios AG, Heilbronn (DE)

( * ) Notice: Subject to any disclaimer, the term of this patent is extended or adjusted under 35 U.S.C. 154(b) by 907 days.

(21) Appl. No.: 16/472,420

(22) PCT Filed: Dec. 11, 2017

(86) PCT No.: PCT/DE2017/000417  
§ 371 (c)(1),  
(2) Date: Jun. 21, 2019

(87) PCT Pub. No.: WO2018/113809  
PCT Pub. Date: Jun. 28, 2018

(65) Prior Publication Data  
US 2019/0366045 A1    Dec. 5, 2019

(30) Foreign Application Priority Data

Dec. 23, 2016 (DE) .................... 10 2016 015 419.5  
May 12, 2017 (DE) .................... 10 2017 004 548.8

(51) Int. Cl.
| | | |
|---|---|---|
| A61B 5/05 | (2021.01) | |
| A61M 25/01 | (2006.01) | |
| A61B 5/0538 | (2021.01) | |
| A61B 5/06 | (2006.01) | |
| A61B 5/00 | (2006.01) | |
| A61M 25/00 | (2006.01) | |

(52) U.S. Cl.  
CPC ....... *A61M 25/0105* (2013.01); *A61B 5/0538* (2013.01); *A61B 5/068* (2013.01); *A61B 5/6852* (2013.01); *A61M 25/005* (2013.01); *A61B 2562/227* (2013.01); *A61M 2025/0166* (2013.01); *A61M 2205/35* (2013.01)

(58) Field of Classification Search  
None  
See application file for complete search history.

(56) References Cited

U.S. PATENT DOCUMENTS

| | | |
|---|---|---|
| 5,235,818 A | 8/1993 | Horikawa et al. |
| 5,314,418 A | 5/1994 | Takano et al. |
| 5,409,487 A | 4/1995 | Jalbert et al. |

(Continued)

FOREIGN PATENT DOCUMENTS

| | | |
|---|---|---|
| CN | 1717262 A | 1/2006 |
| CN | 1758873 A | 4/2006 |

(Continued)

OTHER PUBLICATIONS

International Search Report of PCT/DE2017/000417, dated Apr. 18, 2018.

*Primary Examiner* — Ankit D Tejani  
(74) *Attorney, Agent, or Firm* — Collard & Roe, P.C.

(57) ABSTRACT

A cannula has an electrically conductive material that runs along the cannula. This material has an electrical terminal, which can be wired or wirelessly connected with a measuring device. This makes it possible to acquire the position of the cannula in a human body, and generate a warning signal given a dislocation of the cannula.

16 Claims, 5 Drawing Sheets

(56) References Cited

U.S. PATENT DOCUMENTS

| | | |
|---|---|---|
| 6,951,549 B1 | 10/2005 | Beyerlein |
| 6,973,352 B1 | 12/2005 | Tsutsui et al. |
| 7,251,245 B2 | 7/2007 | Öman |
| 8,265,745 B2 | 9/2012 | Hauck et al. |
| 8,981,225 B2 | 3/2015 | Izawa et al. |
| 9,101,046 B2 | 8/2015 | Sobe |
| 10,111,599 B2 | 10/2018 | Sobe |
| 10,433,747 B2 | 10/2019 | Sobe |
| 10,463,306 B2 | 11/2019 | Maurer et al. |
| 10,729,840 B2 | 8/2020 | Simundic et al. |
| 2004/0176683 A1 | 9/2004 | Whitin et al. |
| 2005/0046303 A1 | 3/2005 | Richard |
| 2006/0173381 A1 | 8/2006 | Eck |
| 2007/0270794 A1 | 11/2007 | Anderson et al. |
| 2008/0243116 A1 | 10/2008 | Anderson |
| 2010/0168735 A1 | 7/2010 | Deno et al. |
| 2013/0030428 A1 | 1/2013 | Worrell et al. |
| 2013/0150824 A1* | 6/2013 | Estes ................ A61M 5/14244 604/151 |
| 2014/0209372 A1 | 7/2014 | Sobe |
| 2015/0045649 A1 | 2/2015 | O'Dea et al. |
| 2018/0110963 A1 | 4/2018 | Simundic |

FOREIGN PATENT DOCUMENTS

| | | |
|---|---|---|
| CN | 101219251 A | 7/2008 |
| CN | 101626724 A | 1/2010 |
| CN | 103415968 A | 11/2013 |
| CN | 104812295 A | 7/2015 |
| CN | 105212902 A | 1/2016 |
| CN | 106132296 A | 11/2016 |
| DE | 102015005002 A1 | 10/2016 |
| EP | 0 484 107 A1 | 5/1992 |
| EP | 0 555 394 B1 | 9/1998 |
| EP | 2 168 479 A2 | 3/2010 |
| GB | 2496025 | 5/2013 |
| JP | 2004-288135 A | 10/2004 |
| JP | 2006-505188 A | 2/2006 |
| JP | 2006-516203 A | 6/2006 |
| JP | 2010-246933 A | 11/2010 |
| JP | 2016-509507 A | 3/2016 |
| JP | 2016-077450 A | 5/2016 |
| WO | 2004/045363 A2 | 6/2004 |
| WO | 2014/118686 A2 | 8/2014 |
| WO | 2016/119771 A2 | 8/2016 |

* cited by examiner

CANNULA HAVING A WIRE THAT EXTENDS ALONG SAID CANNULA

CROSS REFERENCE TO RELATED APPLICATIONS

This application is the National Stage of PCT/DE2017/000417 filed on Dec. 11, 2017, which claims priority under 35 U.S.C. § 119 of German Application No. 10 2016 015 419.5 filed on Dec. 23, 2016 and German Application No. 10 2017 004 548.8 filed on May 12, 2017, the disclosures of which are incorporated by reference. The international application under PCT article 21(2) was not published in English.

The invention relates to a cannula with an electrically conductive material that runs along the cannula.

A cannula with an electrically conductive material, such as a wire, is known from U.S. Pat. No. 5,314,418, for example. The spiral wire here serves to stabilize and shape the cannula. Care is here taken to guide the wire into the cannula in such a way that it not come into contact with a liquid enveloping the cannula. To this end, the wire is guided in particular in the cannula wall. Such a spiral wire also provides kink protection to prevent the flow of fluid from being interrupted.

In principle, the invention can be used for any type of cannulas, to also include needles, ports or shunts. However, it relates in particular to catheters, cannulas with two or more lumens and large cannulas, which are suitable for flows within a range of at least 0.5 to 8 l/min with active pumps, or accesses for lung and heart therapy. Precisely these cannulas portend the danger that the cannula will be pushed out of the blood vessel in the worst case scenario, wherein the patient can die within a few minutes.

The object of the invention is to further develop a cannula with an electrically conductive material that runs along the cannula. This object is achieved with a generic cannula in which the material has an electrical terminal.

To this end, the wire preferably guided in the cannula wall or some other electrically conductive material must be guided out of the cannula or guided toward a cannula wall in such a way as to enable an electrical connection with the material.

The invention is based on the knowledge that such wires used in cannulas or other electrically conductive materials can also be used for transmitting electrical signals, voltages or capacitances. As a consequence, the electrical terminal makes it possible to tap the electrical state in the material and relay it to a measuring or evaluation system.

The electrically conductive material is here formed along the cannula over an area of the length of the cannula that need not encompass the entire cannula. In practice, this area extends roughly from the cannula tip to an area not arranged in a body, making it especially well-suited for including an electrical terminal.

As a consequence, the electrically conductive material in the cannula can connect a sensor with a measuring device, for example. For example, configuring the wire as a thermoelement makes it possible to also transmit temperature values, i.e., voltages corresponding to temperatures. The wire can also be configured in such a way that stretching or bending the wire changes electrical parameters on the wire, as a result of which the electrical terminal can be used to represent changes like these on a measuring device. These measured values can serve to display the parameters or also be used as control parameters.

The material along the cannula can be cylindrical in design. To this end, an area of the cannula can be wound by a band, or a cylindrical element is worked into the cannula or the cannula is enveloped by this element.

A metal is suitable as the electrically conductive material. However, it can also be an electrically conductive plastic or some other electrically conductive material.

In one simple embodiment, the electrically conductive material is a wire.

It is especially advantageous that the wire be spirally wound. As a result, the wire imparts a certain stability to the cannula on the one hand, and the spiral shape allows the wire to act on the entire circumferential surface of the cannula on a specific cannula section on the other. Due to the spiral shape of the wire, the wire can be used as an electrical coil, thereby opening up additional applications, to include in particular the induction of a voltage.

It is advantageous for the cannula to have an outer jacket and inner jacket, between which the electrically conductive material is arranged. The outer jacket and inner jacket can be made out of polyurethane. They can also be integrally fabricated, in particular if the electrically conductive material is incorporated into the cannula wall right away while manufacturing the cannula. As a consequence, a tubular wall preferably comprised of polyurethane can insulate the electrically conductive material radially outwardly and radially inwardly.

The electrical terminal makes it possible to electrically hard wire the cannula with a display, evaluation or control unit. However, a wireless connection is also possible, provided the cannula has a transmitter that is connected with the electrical terminal. The electrical terminal need then not be physically connected with the cannula, but can rather be wirelessly connected with the wire via a transceiver system.

The electrical terminal can be an area of the cannula where the electrical material is easily accessible. This area can be designed as a sliding contact, so that an elongation of the contact can be incorporated in this area.

This sliding contact can be configured as an electrically conductive ring. This makes it possible to use the contact for securing a cable, while the only change to the cannula involves the visible electrical terminal area. This sliding contact can also be configured as a cylindrical or conical sleeve. A conical sleeve makes it easier to simply fasten an open ring to the sliding contact.

A further development provides that the cannula have an RFID element, which is connected in an electrically conductive manner with the electrical terminal. This enables the recording of data on the cannula, and subsequently the wired or wireless transmission of these data to a computer or a console.

Cumulatively or alternatively to the RFID element, a further development can provide that a data memory or data processing device, such as a microchip, be incorporated into the cannula, so as to already process the data acquired with the cannula.

Furthermore, the cannula can also have an additional electrical terminal, which has no electrically conductive connection to the wire. This electrical terminal can serve as a second electrode, and be connected with a contact surface that can come into contact with the skin of a human or animal. It can serve as a second electrode, and hence as an alternative to the EKG patch, so as to realize the connection with the skin, since a capacitor that can be varied depending on the position of the cannula forms between the first electrode, i.e, the electrically conductive material, and the second electrode while using the cannula.

For practical use, it is proposed that the cannula have a cable or plug or bushing, wherein there is an electrically conductive connection between the plug or bushing and the cable, and between the cable and the electrical terminal.

The object underlying the invention is also achieved with a cannula system with the type of cannula having an electrical contact surface that can be fastened to a body surface and a measuring device that is electrically connected with the electrical contact surface and the connection.

Connecting the measuring device with an electrical contact surface and the connection of the wire makes it possible to detect differences in potential between the electrical contact surface and the wire via the measuring device.

In a preferred embodiment, the measuring device serves to determine the electrical capacitance. However, it also possible to determine the Ohmic resistance, an impedance or some other electrical potential or a change in potential.

If the electrical contact surface is immovably fastened to a body surface, the cannula system can be used to determine when the cannula moves relative to the electrical contact surface. This makes it possible to easily recognize a dislocation of a cannula. In particular given a cannula arranged in a vessel, a dislocation can indicate that the cannula has moved out of a vessel. Therefore, it is advantageous if such a dislocation can be determined quickly and easily. Measuring the determined potential or a change in potential makes it possible to precisely indicate how far a positional change in the cannula has progressed. Since a positional change in the cannula usually arises with the cannula in an axial alignment, determining the distance between the cannula and electrical contact surface makes it possible to infer the position of the cannula inside and possibly even outside of a vessel.

The electrical contact surface can also be connected with the measuring device via a transmitter. However, it can also be hard wired with the measuring device in a simple manner.

It is advantageous for the cannula system to have a computer and a signaling device that are connected with the measuring device. As a rule, the computer is arranged in a medical console. If a prescribed electrical measured value is exceeded, this makes it possible to trigger a signal that prompts medical personnel to check the position of the cannula.

Depending on the dislocation, the signaling device can emit various signals and have different signal transmitters, for example for optical or acoustic signals.

The invention also relates to a method for determining the position of a cannula inside of a body part, in which an electrical contact surface is fastened to the body part, and an electrical measured value is determined between the electrical contact surface and a cannula pushed into the body part. Such a method makes it possible to easily monitor the position of the cannula in the vessel. In order to then move the cannula back into the right position in time, it is proposed that the electrical measured value be compared with a reference value, and that an alarm be sounded if the latter is exceeded.

In order to monitor a change in the position of a cannula in a vessel over the long term, it is proposed that the electrical measured value be determined and stored or recorded over a period of time. This makes it possible to uninterruptedly trace whether the cannula is correctly positioned in the vessel.

An exemplary embodiment is shown on the drawing, and will be explained in more detail below. Shown on.

Figures 1, 2, 3:
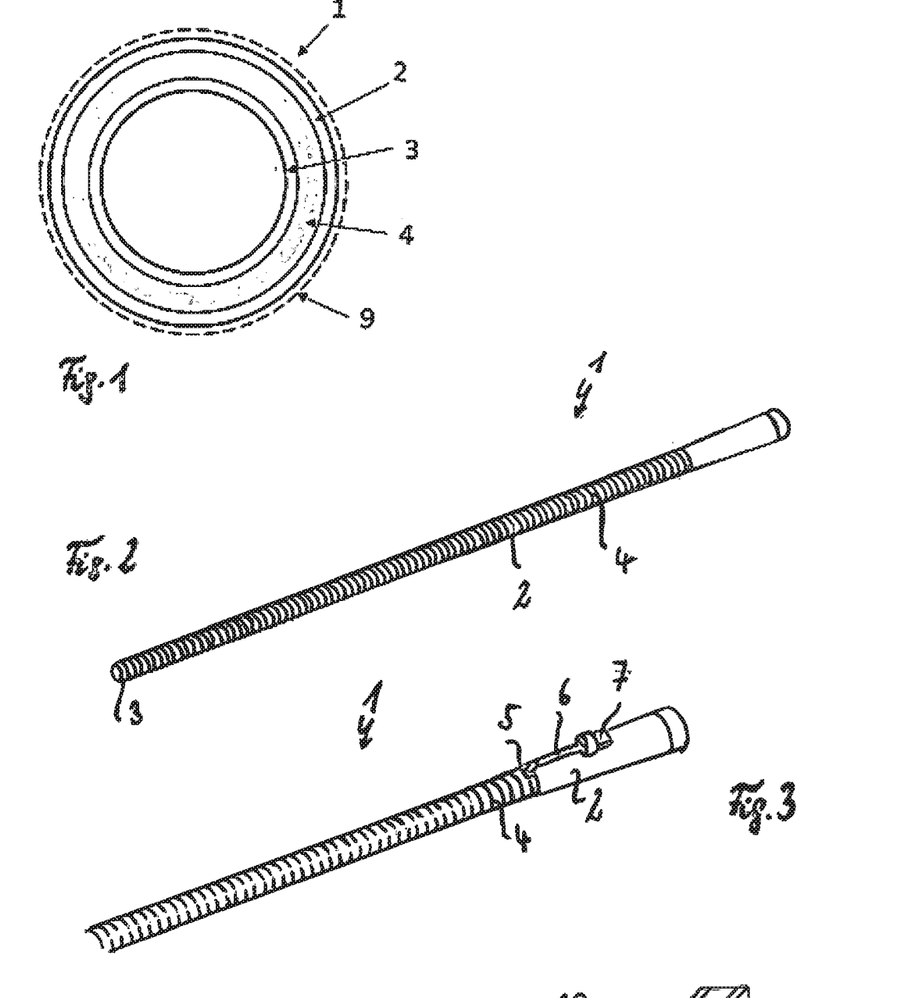
FIG. 1 is a schematic section through a wire-reinforced cannula.
FIG. 2 is a wire-reinforced cannula with electrical terminal.
FIG. 3 is a top view of a wire-reinforced cannula.

The cannula 1 shown on FIG. 1 has a polyurethane outer jacket 2 and a polyurethane inner jacket 3, which comprise an electrical insulation. A wire 4 extending spirally in the longitudinal direction of the cannula is arranged in between as the electrically conductive material.

FIG. 2 shows how the wire 4 is laid around the polyurethane inner jacket 3 in tightly abutting windings visible from outside, and protected by the polyurethane outer jacket 2.

FIG. 3 shows how the wire 4 at one end of the cannula 1 is guided through the polyurethane outer jacket 2 and to the outside, so as to form an electrical terminal 5 at which a cable 6 is used to tap an electrical potential that can be relayed to a measuring device 8 via the plug 7.

Figure 4:
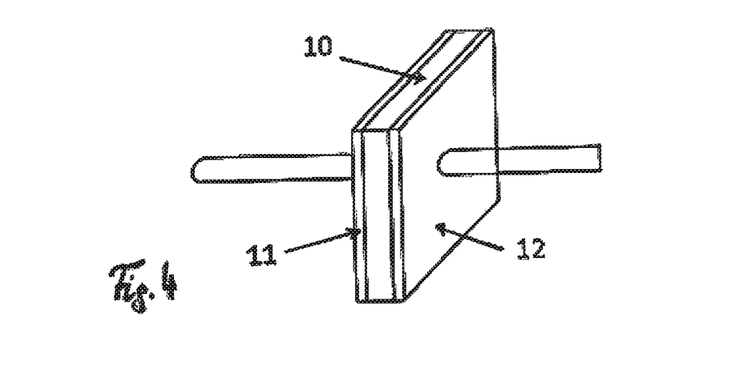
FIG. 4 is a schematic view of an electrical capacitor.

If such a cannula 1 is arranged in a bodily vessel 9, the arrangement acts as an electrical capacitor or an electrical capacitance. FIG. 4 presents a schematic illustration of a capacitor that demonstrates how the polyurethane outer jacket 2 of the cannula 1 acts as a dielectric 10, with the reinforcing wire 4 corresponding to a first electrode 11, and the bodily vessel to a second electrode 12.

Figure 5:
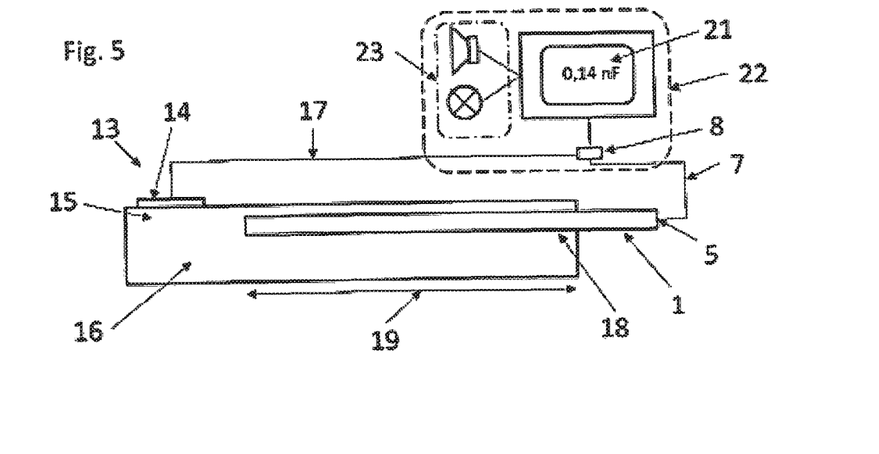
FIG. 5 is a schematic view of a cannula system with cannula, electrical contact surface and measuring device.
Figure 6:
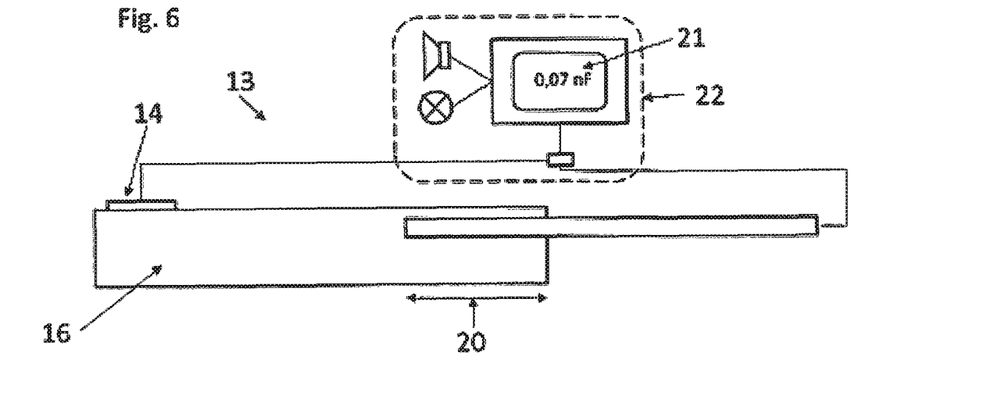
FIG. 6 is the cannula system shown on FIG. 5 with partially withdrawn cannula.
Figure 7:
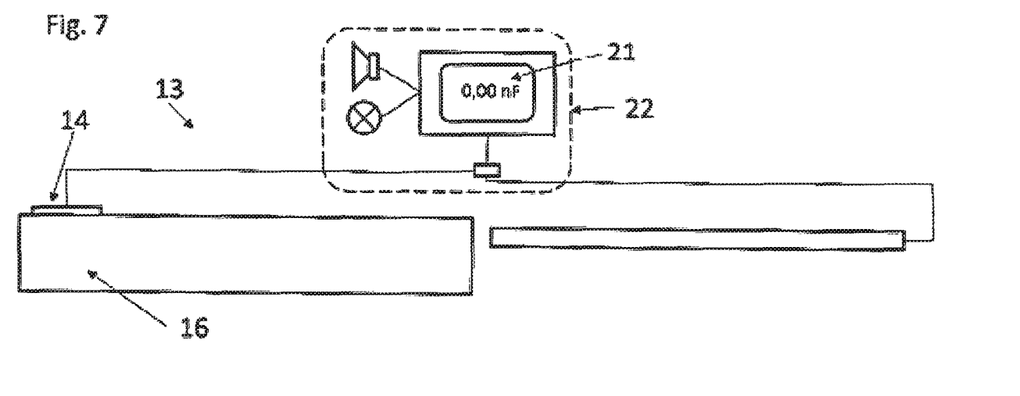
FIG. 7 is the cannula system shown on FIG. 5 with completely withdrawn cannula.

These characteristics of a cannula arranged in a vessel are used in the cannula system 13 shown on FIGS. 5 to 7 to measure the position of a cannula 1 inside of a body part 16 relative to an electrical contact surface 14.

To this end, for example, the electrical contact surface 14 is adhesively bonded to a skin area 15 in proximity to the vessel (not shown) with an EKG patch. The cannula is subsequently positioned in the body part 16, and in particular in a vessel, wherein the cannula 1 is pushed into the proximity of the contact surface 14. The cannula 1 is here connected with the electrical measuring device 8 via the electrical terminal 5 and the line 7, while the electrical contact surface 14 is connected with the measuring device 8 via a line 17.

After the cannula 1 has been optimally positioned via the vessel access 18, the measuring device 8 indicates a value for the measured capacitance. In the exemplary embodiment, this value lies at 0.14 nF. This value is roughly proportional to the length 19 to which the cannula 1 is pushed into the body part 16.

For example, if the cannula is now partially pulled out of the body part 16, and thus out of the vessel, by an awkward movement of the patient, the length 19 is reduced to a length 20, which also reduces the electrical capacitance indicated on the measuring device 8. In the present exemplary embodiment, the length 19 is reduced to roughly half its length 20, with the capacitance dropping from 0.14 nF to 0.07 nF in the process.

FIG. 7 shows a case in which the cannula 1 has been completely pulled out of the body part 16. This causes the measured capacitance to drop to 0.00 nF.

The measured value 21 determined with the measuring device 8 is transmitted to a computer 22, which compares the measured value with a prescribed measured value. Given a drop below a limit, the computer 22 activates a signaling device 23, for example which can emit an optical and/or acoustic signal. The signaling device can also be an alarm or monitoring system of a clinic. As a result, the medical personnel are informed that the position of the cannula should be checked.

The computer 22 can also store the determined measured values over a period of time, so as to comprehensibly demonstrate how the cannula was moved relative to the body part 16.

In addition, the computer 22 can also act on other devices, for example a pump connected with the cannula, for example to stop or reduce the inflow to the cannula when removing the cannula 1 from a vessel.

Figures 8, 9, 10, 11:
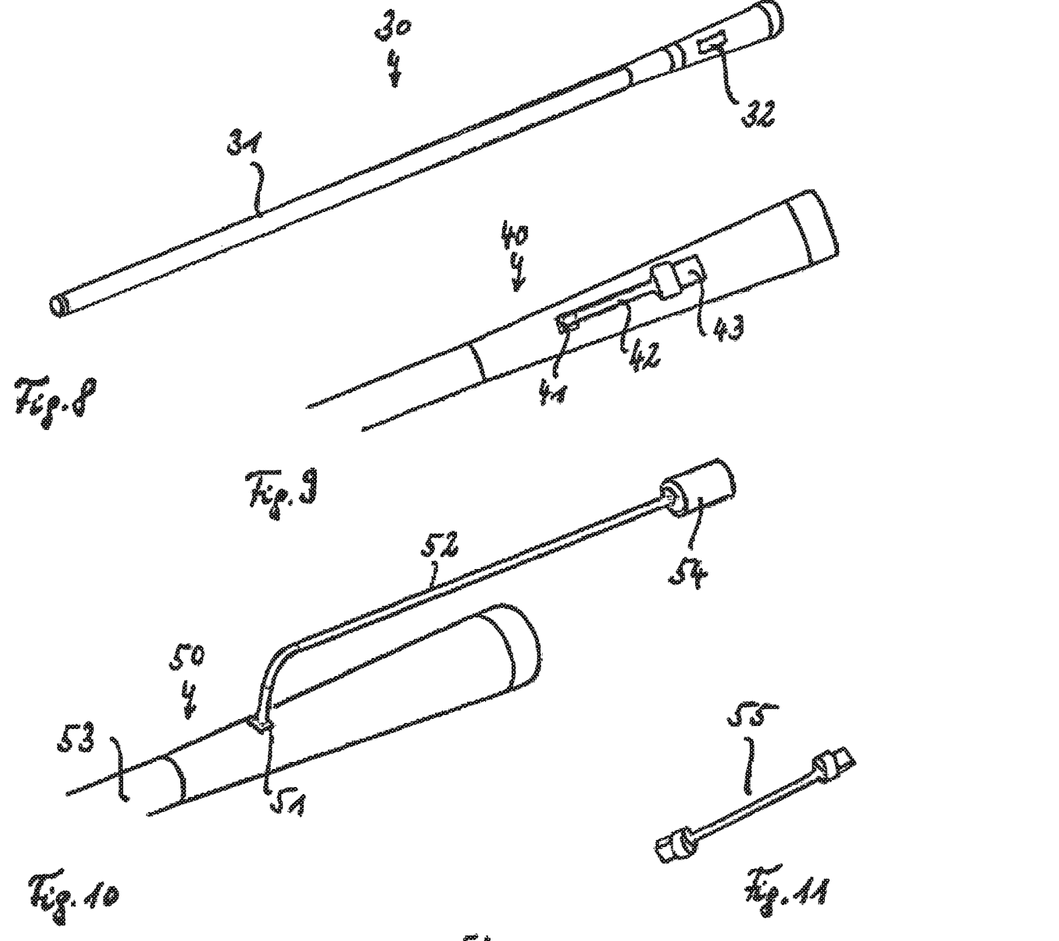
FIG. 8 is a cannula with electrically conductive material cylindrically formed along the cannula.
FIG. 9 is a magnified view of the area of the cannula with electrical terminal shown on FIG. 8 with plug.
FIG. 10 is an alternative embodiment of the cannula with electrical terminal shown on FIG. 8 with bushing.
FIG. 11 is a plug-plug adapter.

FIG. 8 shows a cannula 30 with an electrically conductive material 31 cylindrically formed along the cannula and an RFID chip 32. This RFID chip 32 with its connection to the material 31 is incorporated insulated inside of the cannula, and the RFID chip is arranged on the cannula in such a way as to be located outside of the body when positioning the cannula in a body.

FIG. 9 shows a cannula 40 with an electrical terminal 41, onto which a cable 42 is soldered. The cable 42 has a plug 43, which is used for connecting to the measuring device 8.

FIG. 10 presents an alternative embodiment of the cannula 50. The cable 52 is here lengthened, and is connected with the electrically conductive material 53 via the electrical terminal 51. The end of the cable 52 has a bushing 54, which can also be used as a plug via the adaptor 55 depicted on FIG. 11.

Such cannulas can be easily manufactured, so as to also be used as disposables.

Figure 12:
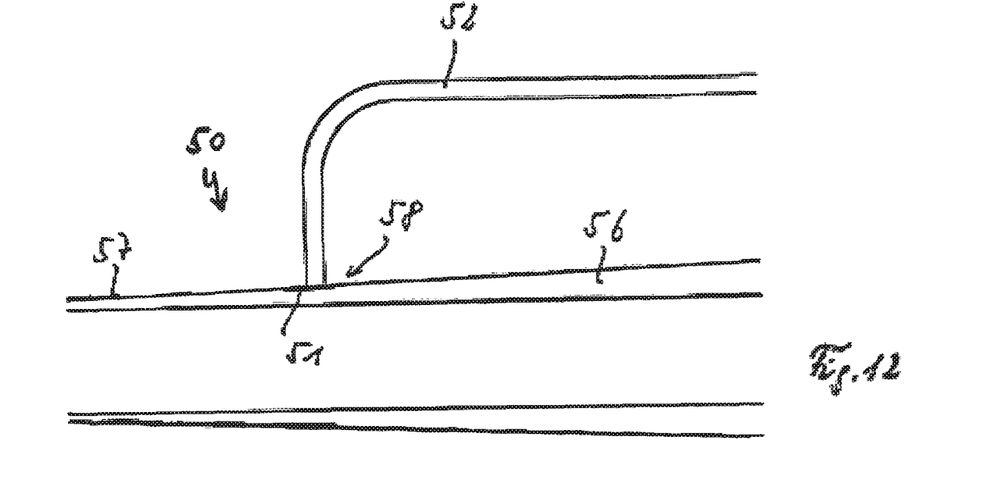
FIG. 12 is a magnified view of the areas of the electrical terminal.
Figure 13:
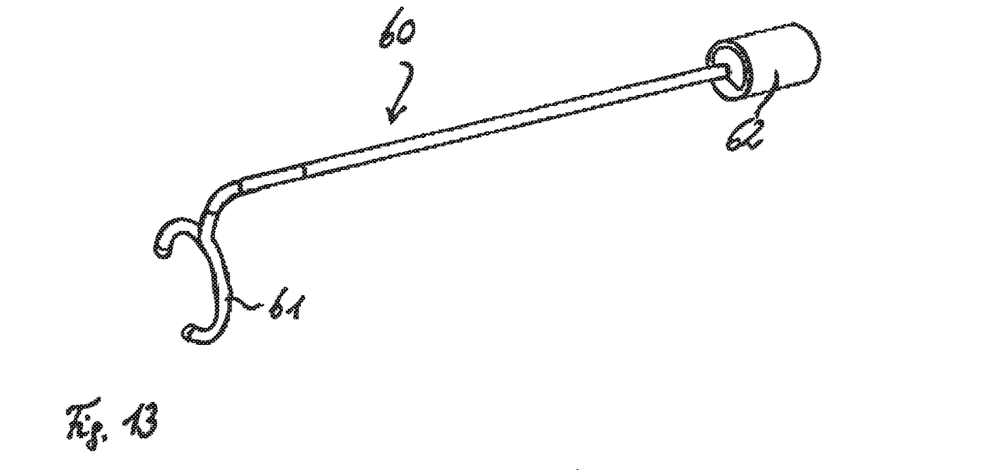
FIG. 13 is a cable with ring holder and bushing.
Figure 14:
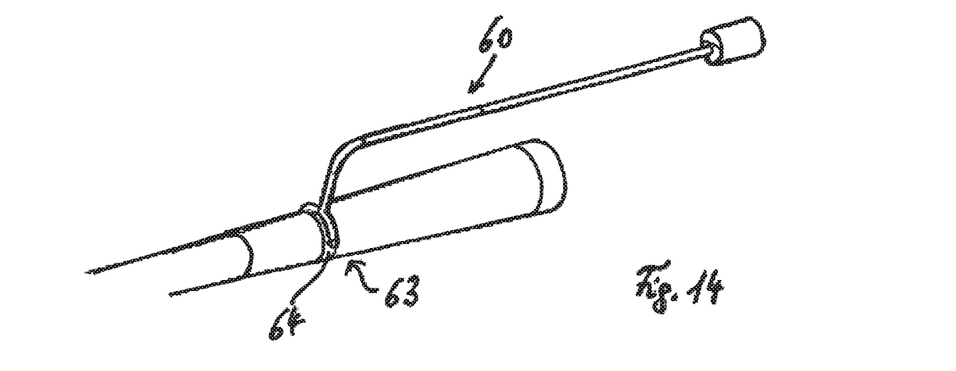
FIG. 14 is the cable shown on FIG. 13 on the cannula.

FIG. 12 shows a section of a cannula 50 consisting of a polyurethane material 56. Attached to the material 56 is a metal cannula reinforcement 57, which serves as a sensor element and is integrated into the cannula wall in such a way as to be electrically insulated to the outside and inside. An accessible metal electrically conductive area 58 in the cannula surface comprised of biocompatible material is electrically connected with the sensor element. The cable 52 is soldered onto this electrical terminal 51.

Instead of soldering a cable 52 onto a contact 51, the embodiment variants shown on FIGS. 13 to 17 provide a cable 60 with a slip ring 61 and a bushing 62, which is designed as a reusable unit that can be disinfected and, in autoclaves, sterilized.

Figure 15:
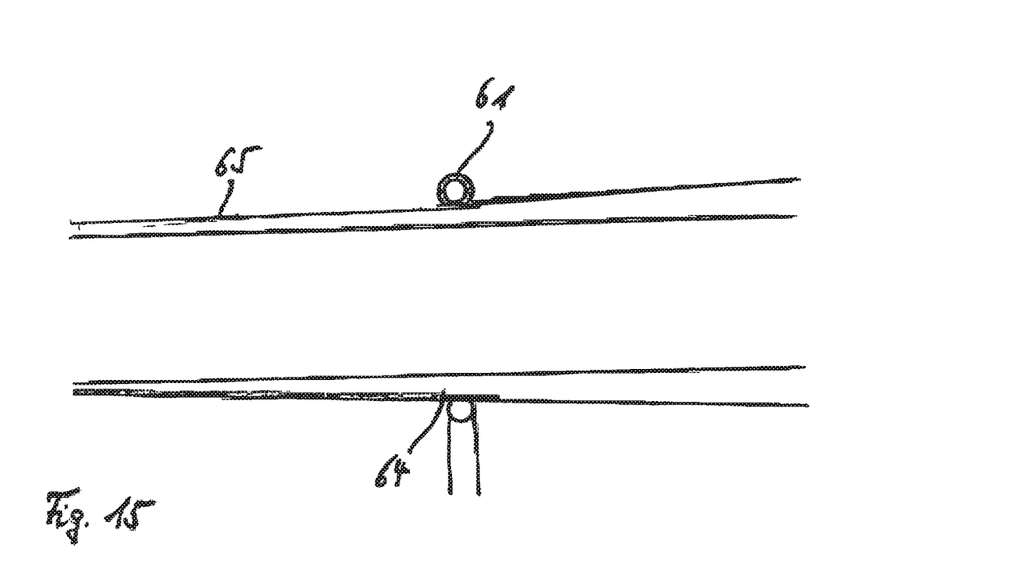
FIG. 15 is a magnified section through the area where the cable abuts against the cannula.

This cable 60 can be easily secured via the slip ring 61 with an electrically conductive ring 63 having a conical sleeve 64. FIG. 15 shows how the ring 61 can be slipped onto the conical sleeve 64, so as to there enable an electrical contact between the electrically conductive material 65 and the cable 60 via the ring 61.

Figure 16:
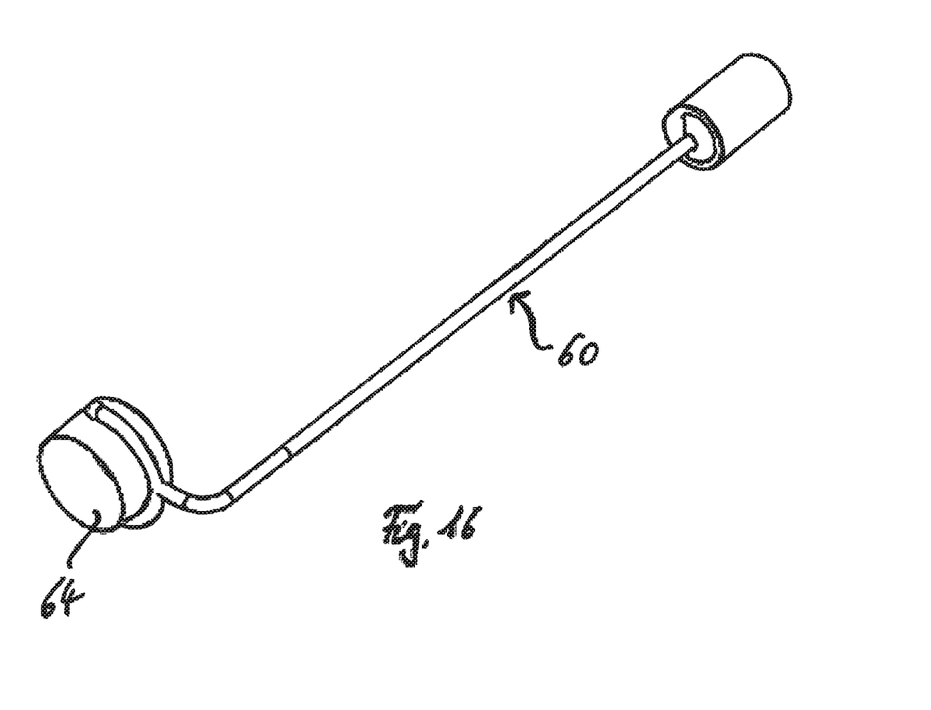
FIG. 16 is the interaction between the cable shown on FIG. 13 and an electrically conductive ring as part of the cannula.
Figure 17:
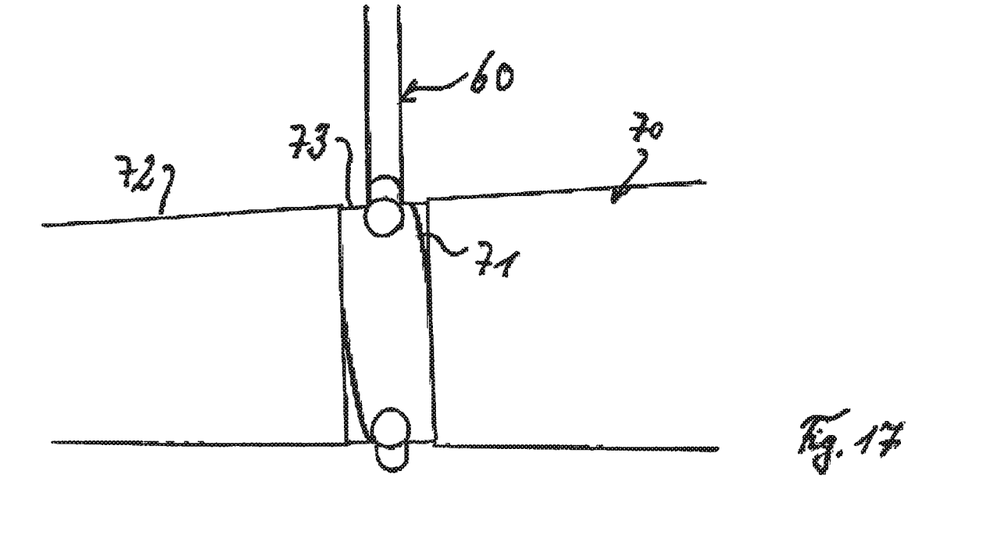
FIG. 17 is the interaction between the cable shown on FIG. 13 and a cannula according to FIG. 3 with a spiral wire.

FIG. 16 shows how the cable 60 is fastened to a ring 64 detached from the cannula. As an alternative, the ring 61 can also interact directly with a wire 71 spirally guided in a cannula 70 in an area 73 with insulation 72 removed.

The invention claimed is:

1. A cannula with an electrically conductive material that runs along the cannula,
    wherein the material has an electrical terminal;
    wherein the cannula has an outer jacket and an inner jacket, which are electrically insulating, and between which the electrically conductive material is arranged such that the electrically conductive material is guided in a cannula wall and radially outwardly and radially inwardly insulated by a tubular wall;
    wherein the electrically conductive material extends in the cannula wall over an area along the cannula from the cannula tip to the electrical terminal; and
    wherein the cannula is adapted such that, when arranged in a body vessel, the outer jacket of the cannula acts as a dielectric, with the electrically conductive material corresponding to a first electrode, and the body vessel to a second electrode, such that the position of the cannula inside of a body part relative to an electrical contact surface can be measured.

2. The cannula according to claim 1, wherein the material is cylindrical in design along the cannula.

3. The cannula according to claim 1, wherein the material has a wire.

4. The cannula according to claim 3, wherein the wire is spirally wound.

5. The cannula according to claim 1, wherein the cannula has a transmitter that is connected with the electrical terminal.

6. The cannula according to claim 1, wherein the electrical terminal has a sliding contact.

7. The cannula according to claim 6, wherein the sliding contact is designed as an electrically conductive ring.

8. The cannula according to claim 7, wherein the electrically conductive ring is designed as a conical sleeve.

9. The cannula according to claim 1, wherein the cannula has an RFID element, which is connected with the electrical terminal in an electrically conductive manner.

10. The cannula according to claim 1, wherein the cannula has another electrical terminal that has no electrically conductive connection to the wire.

11. The cannula according to claim 1, wherein the cannula has a cable and a plug or a bushing, wherein there is an electrically conductive connection between the plug or the bushing and the cable, and between the cable and the electrical terminal.

12. A cannula system with the cannula according to claim 1, further comprising an electrical contact surface that can be fastened to a body surface and a measuring device that is electrically connected with the electrical contact surface and the terminal.

13. The cannula system according to claim 12, wherein the measuring device is a measuring device for determining the electrical capacitance.

14. The cannula system according to claim 12, wherein the electrical contact surface has a transmitter.

15. The cannula system according to claim 12, wherein the cannula system has a computer and a signaling device which are connected with the measuring device.

16. The cannula system according to claim 15, wherein the signaling device has several different signal transmitters.

* * * * *